United States Patent [19]

Egyud

[11] 4,066,650
[45] Jan. 3, 1978

[54] KETO-ALDEHYDE-AMINE ADDITION PRODUCTS AND METHOD OF MAKING SAME

[76] Inventor: Laszlo G. Egyud, 12 Redgate Lane, Quissett, Falmouth, Mass. 02543

[21] Appl. No.: 552,881

[22] Filed: Feb. 25, 1975

Related U.S. Application Data

[63] Continuation of Ser. No. 114,680, Feb. 11, 1971, abandoned.

[51] Int. Cl.² .................. C07D 213/69; C07D 207/44
[52] U.S. Cl. ........................ 260/281 G; 260/239 A; 260/293.69; 260/293.71; 260/293.63; 260/326 A; 260/326 NS; 260/326.5 FM; 260/347.7; 260/586 M; 260/593 R; 424/244; 424/267; 424/274
[58] Field of Search ..... 260/281 R, 281 G, 326.5 FM

[56] References Cited
FOREIGN PATENT DOCUMENTS 76,165   9/1954   Netherlands .............. 260/326.5 FM

*Primary Examiner*—Paul M. Coughlan, Jr.
*Assistant Examiner*—Mark L. Berch
*Attorney, Agent, or Firm*—Michael J. Striker

[57] ABSTRACT

Addition products of a mono-substituted keto-aldehyde compound with a secondary amine. The compounds have the formula

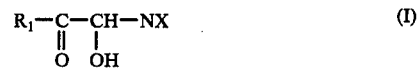

wherein $R_1$ stands for various organic radicals as defined in the body of the specification and X is a 4-, 5- or 6-member ring or fused double ring which includes a nitrogen atom in the ring attached to the keto-aldehyde group and wherein the latter ring is substituted by =O in the two positions ortho to said nitrogen atom.

The compounds are anti-bacterial, anti-viral and anti-neoplastic agents and are valuable in connection with combatting the rejection mechanism in transplantations. They are furthermore useful as radiosensitizers in connection with radiation treatments for various purposes.

2 Claims, No Drawings

KETO-ALDEHYDE-AMINE ADDITION PRODUCTS AND METHOD OF MAKING SAME

This is a continuation, of application Ser. No. 114,680, filed 02/11/1971, now abandoned.

BACKGROUND OF THE INVENTION

The invention relates to addition products between α-keto-aldehydes and secondary amines α-keto-aldehydes are well known and usually are prepared through oxidation (Riley, H. L., Morley, J. F., and Friend, N.A.C.: J.Chem.Soc. 1932.1875; Rabjohn, N.: in Organic Reactions 5.331.1949; and Waitkins, G. R., and Clark, C. W.: Chem.Rews 36, p. 235, 1945) of the active methylene groups to carbonyl groups by means of selenous acid ($H_2SeO_3$). It has also been known that these α-keto-aldehydes are potential inhibitors of in vitro and in vivo cell division (Egyud, L. G.: Proc.Natl.Acad.Sci. 54, p. 200, 1965; Egyud, L. G. and Szent-Györgyi, A.: Proc.Natl.Acad.Sci. 55, p. 388, 1965; Szent-Györgyi, A., Egyud, L. G., and McLaughlin, J.: Sci. 155, p. 359, 1967; Egyud, L. G.: Curr.Mod.Biol. 1, p. 14, 1967; Egyud, L. G., and Szent-Györgyi, A.: Proc.Natl.Acad. Sci. 56, p. 203, 1966; Egyud, L. G., and Szent-Györgyi, A.: Sci. 160, p. 1140, 1968; Apple, M. A., and Greenberg, D. M.: Can.Chem.Ther.Rep. 51, p. 455, 1967; Kenny, C. P., and Sparkes, B. G.: Sci. 161, p. 1344, 1968; Sparkes, B. G. and Kenny, C. P.: Proc.Natl.Acad.Sci. 64, P. 920, 1969; Gregg, C. T.: Eptl.Cell Res. 50, p. 65, 1968; and Scaife, J. F.: Experientia 25, p. 178, 1969).

The α-keto-aldehydes are further known as potent anti-viral agents (Baylor, M., and Egyud, L. G.: Virology 31, p. 380, 1967; De Bock, C. A. in Nature 179, p. 706, 1957; Cavallini, C. et al. in J. Medicinal Pharamceut. Chem. 1, p. 365, 1959; Engle, C. C. et al. in J.Immunol. 89 531, 1962; Underwood, C. R. et al. in Proc.Soc.Exptl.Biol.Med.; 93, p. 421, 1956; Tiffany, B. D. et al. in J.Amer.Chem.Soc. 79, 1682, 1957). In recent research the inhibition of cell division with α-keto-aldehydes has been related to the blocking of protein synthesis (Otsuka, H. and Egyud, L. G.: Can.Res. 27, p. 1498, 1967; and Otsuka, H. and Egyud, L. G.: Curr.Mod.Biol. 2, p. 106, 1968). Cancer cells have been shown to possess an increased sensitivity to α-keto-aldehydes which may be explained by a specific reaction between the keto-aldehydes and guanine residues present in the excessive amounts of s-RNA-s in the cell (Shapiro, R.: Ann.N.Y.Acad.Sci. 163, art. 2, p. 624, 1969; Shapiro, R. and Hachmann, J.: Biochem. 5, p. 2799, 1966; and Litt, M. and Hancock, F.: Biochem. 6, p. 1848, 1967).

However, these α-keto-aldehydes exhibit a relatively high toxicity in animals. They are moreover readily metabolized to the corresponding β-hydroxy acids by glyoxalases, the enzyme system that is ever-present in all living cells.

The inhibitory action of the α-keto-aldehydes on cell division is furthermore reversed upon addition of thiols (Egyud, L. G.: Curr.Mod.Biol. 2, p. 128, 1968).

It is therefore an object of the present invention to modify the α-keto-aldehydes in a manner such that they are protected against the action of glyoxalases while at the same time their in vivo toxicity is decreased and their tumor specificity is enhanced. The incorporation of a blocking group as indicated in the α-keto-aldehydes is known as "latentiation". In a general way, the latentiation of the α-keto-aldehydes is thus the object of the present invention.

SUMMARY OF THE INVENTION

This object is accomplished by the addition reaction between an α-keto-aldehyde and a secondary amine, this reaction resulting in an N-substituted tertiary amine in which the aldehydic function of the dicarbonyl residue forms the anchoring point for the tertiary amine group. The compounds of the invention accordingly have the formula

where $R_1$ is a. straight or branched, saturated or unsaturated aliphatic alkyl of 1 to 11 carbon atoms, b. an alicyclic group of 3 to 6 carbon atoms, c. an aromatic group having 5 to 6 carbon atoms in the ring structure and including from 1 to 2 rings, d. an aromatic group as defined at (c) which includes from 1 to 2 hetero atoms consisting of nitrogen, oxygen, e. a steroid residue, or f. a group as defined at (a) to (e) which is substituted by chlorine, nitro, hydroxy, alkoxy or a phosphate group, and wherein X is a 4-, 5- or 6-member ring or fused double ring which includes a nitrogen atom in the ring attached to the keto-aldehyde group and wherein the latter ring is substituted by =O in the two positions ortho to said nitrogen atom.

The invention also embraces a method for making the products wherein an α-keto-aldehyde which is mono-substituted by the desired radical is reacted with a cyclized secondary amine at elevated temperature and in solution.

The invention furthermore relates to pharmaceutical compositions comprising a compound as defined and a suitable diluent therefor.

The invention furthermore includes the method of combatting a rejection mechanism preceding or following a transplantation of tissue or organs, the said method comprising administering to the human patient or animal a compound as previously defined.

The invention furthermore relates to a method of treating a human patient or animal suffering from a neoplastic growth with the compounds as defined for the purpose to arrest or destroy the growth.

DESCRIPTION OF THE PREFERRED EMBODIMENTS

The addition reaction of the present invention is based on the finding that the nitrogen atom in certain secondary amines, and particularly in dicarboxylic acid imides, reacts readily with the aldehydic group of the keto-aldehyde, resulting in the mono-substituted derivative defined above.

The general method of the invention may be described by reference to the reaction of the acid imides as follows:

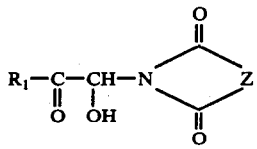

In formula (II) Z may for instance be: —CH₂—, —CO—, —CH(OH)—, —CH(CH₃)—, —C(CH₃)₂—, —CH(CH₂CH₃)—, —CH₂—CH₂—, —CH(OH)—CH₂—, —C(O)—CH₂—, —CH(CH₃)—CH₂—, —C(OH)₂—CH₂—, —C(=CH₂)—CH₂—, —C(CH₃)₂—CH₂—, —C(OH)(CH₃)—CH₂—, —CH(OH)—CH(OH)—, —C(O)—C(O)—, —CH(CH₃)—CH(CH₃)—, —CH=CH—, —C(OH)=CH—, —C(CH₃)=CH—, —C(OH)=C(OH)—, —C(CH₃)=C(CH₃)—, —CH₂—CH₂—CH₂—, —C(O)—CH₂—CH₂—, —CH₂—C(O)—CH₂—, CH(OH)—CH₂—CH₂—, —CH₂—CH(OH)—CH₂—, —CH(CH₃)—CH₂—CH₂—, —CH₂—CH(CH₃)—CH₂—, —CH=CH—CH₂—, —C(OH)=CH—CH₂—, —CH=C(OH)—CH₂—, —C(CH₃)=CH—CH₂— or —CH=C(CH₃)—CH₂—.

Accordingly, Z forms part of a 4-, 5- or 6-membered ring together with the —C(O)—NH—C(O)— function and may include additional substituents on various carbon atoms, such as:

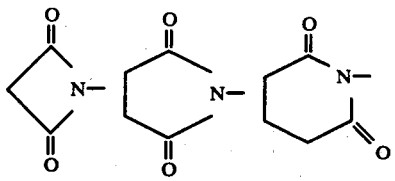

The 5- and 6-membered ring structures may also contain a C=C group positioned between the two —C(O)— functions in case of the 5-membered ring and, in case of the 6-membered ring, in α-position to one of the —C(O)— functions, such as:

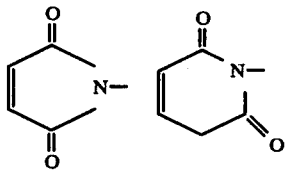

Merely for purposes of illustration, the general course of the reaction may be about as follows:

0.1 mole of the dicarboxylic acid-imide was suspended in 100–400 ml of distilled water or in a mixture of 200 ml water and 200 ml of p-dioxane containing a trace amount of K₂CO₃. The mass was heated to 70° C upon constant stirring. As soon as the solution was complete, 0.11 mole of α-keto-aldehyde (dissolved in water or 50% aqueous p-dioxane, about 40% weight per volume) was added in one batch, and the reaction mixture was maintained at 70° C for another 0.5–4 hours. At the end of the reaction time, the mixture was filtered through folded paper while hot, cooled to room temperature and concentrated in a vacuum to a thick syrup.

The thick syrup was digested with ether at room temperature. The ether-insoluble solid was collected on filtration and was washed with a small quantity of ice cold ether and dried at room temperature. The resultant crude solid was recrystallized twice from hot benzene or, in a few instances, some suitable solvent, such as water or a mixture of ethanol and benzene. A small amount of gummy material that remained undissolved in benzene was removed on filtration before crystallization.

The recrystallized crystalline material was dried over silica gel in a vacuum at 30°–40° C. The overall yield was between 30 and 55% of the theoretical yield.

STARTING PRODUCTS

The α-keto-aldehydes may be obtained in conventional manner from the corresponding aldehydes or 2-ketones with selenous acid, as appears from the following two reactions $$R_1CH_2CHO \rightarrow R_1—COCHO \qquad (III)$$

$$R_1CH_2—CO—CH_3 \rightarrow R_1CH_2COCHO + R_1—CO—CO—CH_3 \qquad (IV)$$

$R_1$ in these reactions is an organic radical as defined above.

A single product was obtained with the method of reaction (III), although the oxidation in that case is somewhat sluggish. The oxidation proceeds more smoothly and rapidly with the method of equation (IV) but, in addition to the desired α-keto-aldehyde, a by-product, the 2,3-diketone is formed at least in those cases where a methylene group for the reaction is available.

The relative yield of the α-keto-aldehyde and the 2,3-dicarbonyl is greatly dependent on the specific conditions during oxidation.

The α-keto-aldehyde is then purified and isolated by preparative gas chromatography, for instance in an aluminum column filled with 20% "Carbowax C-20M" on HMDS treated Chromosorb W (80-100 mesh) with N₂ as carrier gas. Most of the keto-aldehydes which will be listed below were synthesized with selenous acid in the manner just described. This applies also to the progesterone-21-aldehyde in which case progesterone was oxidized with selenous acid. However, cortisone-21-aldehyde and cortisol-21-aldehyde were prepared by cupric acetate oxidation of the corresponding steroids.

A number of compounds are available from commercial sources, such as methylglyoxal (technical grade) and phenylglyoxal as well as hydroxymethylglyoxal. For instance, β-substituted α-keto-butyraldehydes are available under the tradenames "Kethoxal" and "Methoxal".

The following is a list of α-keto-aldehydes which can be used in the present reaction.

methylglyoxal (1-oxopropanal) - CH₃—CO—CHO
ethylglyoxal - CH₃—CH₂—CO—CHO
propylglyoxal - CH₃—(CH₂)₂—CO—CHO
butylglyoxal - CH₃—(CH₂)₃—CO—CHO
pentylglyoxal - CH₃—(CH₂)₄—CO—CHO
hexylglyoxal - CH₃—(CH₂)₅—CO—CHO
heptylglyoxal - CH₃—(CH₂)₆—CO—CHO
octylglyoxal - CH₃—(CH₂)₇—CO—CHO
nonylglyoxal - CH₃—(CH₂)₈—CO—CHO
decylglyoxal - CH₃—(CH₂)₉—CO—CHO
undecylglyoxal - CH₃—(CH₂)₁₀—CO—CHO
vinylglyoxal - CH₂=CH—CO—CHO

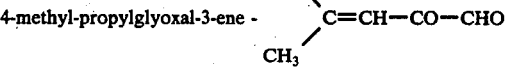

4-methyl-propylglyoxal-3-ene

-continued isobutylglyoxal - $(CH_3)_2CH-CH_2-CO-CHO$ cyclopropylglyoxal - ▷CH—CO—CHO 2-furylglyoxal - (furyl)—CO—CHO 5-hydroxypropylglyoxal - HO—CH₂—CH₂—CH₂—CO—CHO phenylglyoxal - (C₆H₅)—CO—CHO 2,5-dichlorophenylglyoxal - (2,5-Cl₂C₆H₃)—CO—CHO 4-biphenylglyoxal - (biphenyl)—CO—CHO pyridine-2-glyoxal - (pyridin-2-yl)—CO—CHO pyridine-3-glyoxal - (pyridin-3-yl)—CO—CHO pyridine-4-glyoxal - (pyridin-4-yl)—CO—CHO p-nitrophenylglyoxal - NO₂—(C₆H₄)—CO—CHO 1-chloromethylglyoxal - Cl—CH₂—CO—CHO 1,1-dichloromethylglyoxal - Cl₂CH—CO—CHO hydroxymethylglyoxal - HO—CH₂—CO—CHO α-keto-β-ethoxy-butyraldehyde ("Kethoxal") - $CH_3-CH(OCH_2CH_3)-CO-CHO$ α-keto-β-methoxy-butyraldehyde ("Methoxal") - $CH_3-CH(OCH_3)-CO-CHO$ Keto-aldehydes formed by substitution of the methyl or methylol (—CH₂—OH) group on steroids are, for instance, the following:

progesterone-21-aldehyde
(progesterone-17-α-keto-aldehyde)

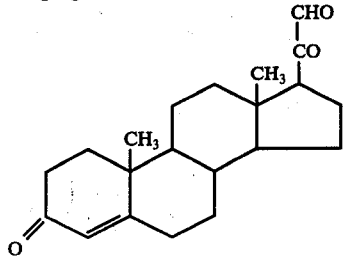

cortisone-21-aldehyde
(cortisone-17-α-keto-aldehyde)

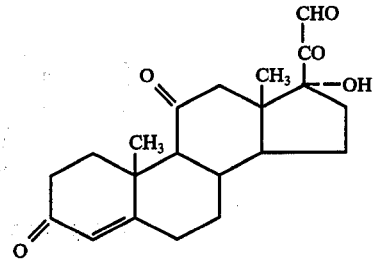

cortisol-21-aldehyde
(cortisol-17-α-keto-aldehyde)

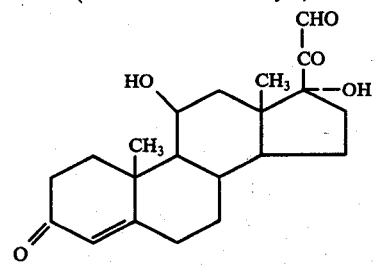

The secondary amines which are reacted with the keto-aldehydes can be, broadly, any secondary amines as defined above. As an illustration, the following compounds may be listed:

maleimide
(2,5-dioxo-Δ³-pyrroline)

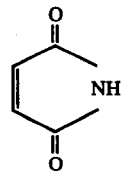

glutaconic imide
(2,6-dioxo-Δ³-pyridine)

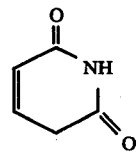

malonimide
(2,4-dioxo-azetidine)

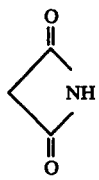

glutarimide
(2,6-dioxo-pyridine)

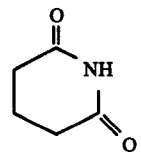

succinimide
(2,5-diketopyrrolidine)

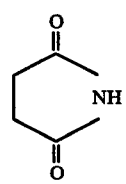

phthalimide
(1,3-isoindoledione)

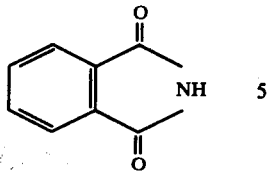  5

ILLUSTRATIVE PRODUCTS OF THE INVENTION

Since the reaction of the present invention proceeds, broadly, between the α-keto-aldehydes and the secondary amines, it will be understood that reacting the above-listed keto-aldehydes with different secondary amines as listed above will result in a large number of different compounds. Merely for purposes of illustration, the formulae of the compounds resulting from the reaction of various α-keto-aldehydes as above listed with either maleimide or glutaconic imide are listed hereunder.

In these formulae Y therefore is either

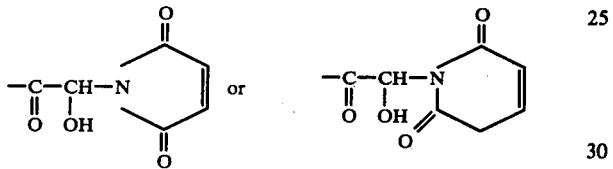

The compounds accordingly are
CH$_3$—Y
CH$_3$—CH$_2$—Y
CH$_3$—(CH$_2$)$_2$—Y
CH$_3$—(CH$_2$)$_3$—Y
CH$_3$—(CH$_2$)$_4$—Y
CH$_3$—(CH$_2$)$_5$—Y
CH$_3$—(CH$_2$)$_6$—Y
CH$_3$—(CH$_2$)$_7$—Y
CH$_3$(CH$_2$)$_8$—Y
CH$_3$—(CH$_2$)$_9$—Y
CH$_3$(CH$_2$)$_{10}$—Y
CH$_2$=CH—Y

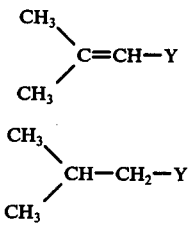

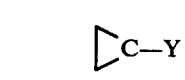

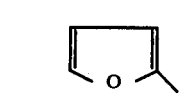

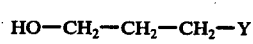

HO—CH$_2$—CH$_2$—CH$_2$—Y

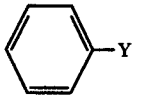

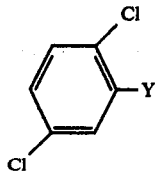

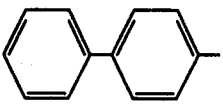

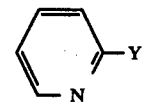

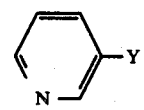

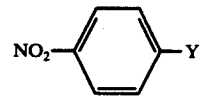

Cl—CH$_2$—Y

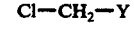

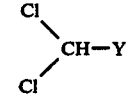

HO—CH$_2$—Y

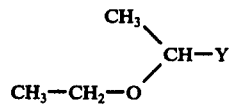

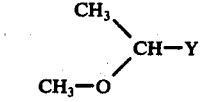

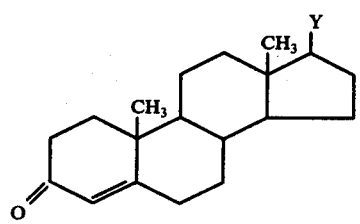

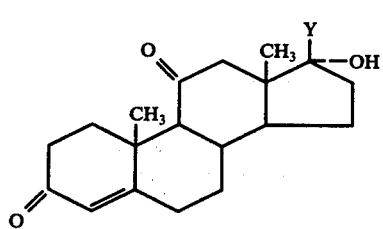

-continued

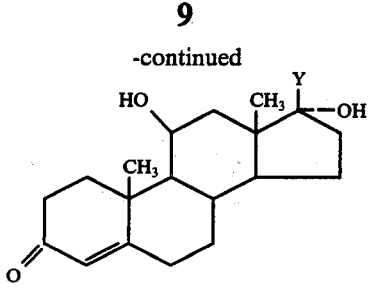

As a further illustration a few specific compounds may be listed with their formulas fully spelled out:

For instance, methylglyoxal which is "latentiated" with maleimide gives the following compound

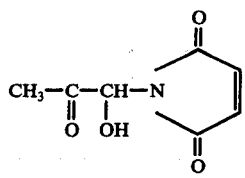

Pentylglyoxal reacted with maleimide gives the following compound

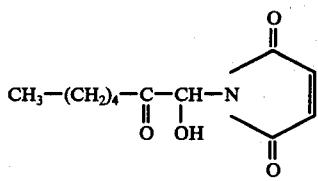

Progesterone-17-α-keto-aldehyde latentiated with glutaconic imide results in the following compound:

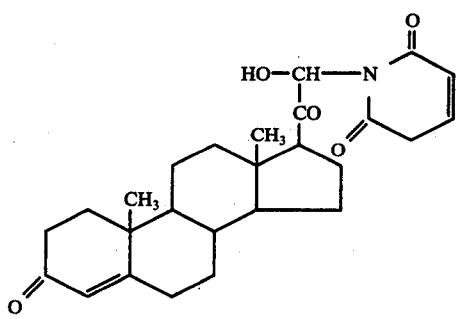

"Methoxal" (α-keto-β-methoxy-butyraldehyde) reacted with succinimide results in the following compound

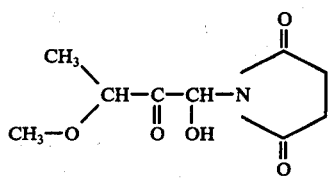

METHOD OF MAKING THE COMPOUNDS

The following examples will further illustrate the invention. In all of these examples methylglyoxal is reacted with different dicarboxylic acid imides It should be understood that the conditions of the reaction with other α-keto-aldehydes, particularly the keto-aldehydes listed above, would be basically the same.

EXAMPLE I

Methylglyoxal-malemide

N'-(2-keto-propane-1-ol)-2,5-dioxopyrroline-3-ene.
Reaction:

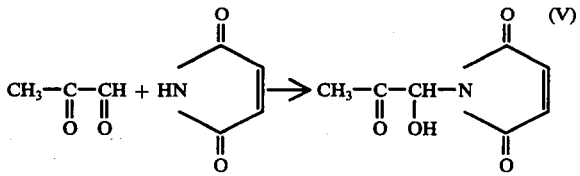

9.7 g. of maleimide were added to 100 ml of water containing trace amounts of $K_2CO_3$. The pH of the suspension was adjusted to 5.0 with alkali (KOH). The mixture was heated to 70° C while stirring. When all solid had dissolved, 20 ml (8.0 g) of 40% aqueous methylglyoxal were added in one batch and the reaction mixture was kept at 70° C while stirring for another half hour.

During the heating the yellow reaction mixture darkened to a reddish-brown color.

At the end of the reaction time the solution was filtered through folded paper, cooled to room temperature and concentrated to a thick syrup in a vacuum. The thick syrup was digested with diethylether at room temperature and the insoluble brownish-yellow precipitate was collected by filtration. It was washed with a small amount of ice-cold ether and suction-dried. The suction-dried solid was taken up in hot benzene, rapidly filtered to remove a small amount of insoluble gum of brown color and cooled on ice. The pale yellow crystalline solid was collected, washed with a small amount of cold benzene and suction-dried. The crystals finally were dried over silica gel at 40° C in a vacuum.

Yield: 11.0 g (69.1% of theoretical)
Analysis: mp: 80°–81° C.

|     | theoretical | found |
| --- | --- | --- |
| C%  | 49.71 | 49.68 |
| H%  | 4.17  | 4.30  |
| N%  | 8.28  | 8.22  |
| O%  | 37.84 | 37.70 |

The IR-spectra, NMR confirmed the structure. With mass-spectroscopy the compound showed immediate fragmentation even at 15 eV. The highest molecular peak observed was at mass 126 instead of the expected mass 169 which is in agreement with the formula

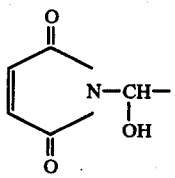

The degradation product of mass 43 corresponding to the —C(O)—CH₃ structure also appeared as a major peak on the spectra.

EXAMPLE II

Methylglyoxal-glutaconic imide

N'-(2-keto-propane-1-ol)-2,6-dioxopyridine. Reaction:

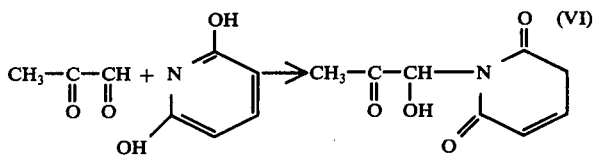

In this example 2,6-dihydroxy-pyridine was used as the latentiating agent.

2,6-dihydroxy-pyridine is a desmotrope of glutaconic imide (Beilstein: Handbuch of Organic Chemistry 21. p. 406):

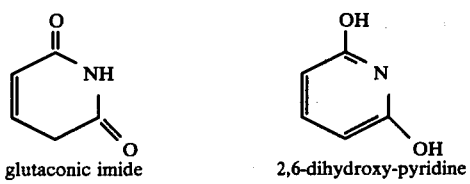

glutaconic imide     2,6-dihydroxy-pyridine 14.75 g of 2,6-dihydroxypyridine HCl were suspended in 400 ml of water and the pH was adjusted to 5.5 with alkali (KOH) and a trace amount of $K_2CO_3$ was added. The mixture was heated to 70° C while stirring. When all solids had dissolved to form a greenish solution, 20 ml (8.0 g) of 40% aqueous methylglyoxal was added in one batch, and the reaction mixture was kept at 70° C for another half hour.

Within 5 minutes after the addition of the keto-aldehyde the reaction mixture became a deep purple-violet in color which color persisted throughout the reaction.

At the end of the reaction time the solution was filtered through folded paper, cooled to room temperature and concentrated to a thick syrup in a vacuum. The thick syrup was digested with diethylether at room temperature. The precipitated violet-colored crystals were collected on filtration washed with diethylether and dried by suction. The crude product was purified by recrystallization from a mixture of ethanol and ether. The solid was dissolved in small volume of hot ethanol, filtered, rapidly cooled to room temperature and several volumes of ether were added. Crystals formed on storage at −5° C. Finally the crystals were dried over silica gel in a vacuum at 40° C.

Yield: 10.0 g. (55.0% of theoretical)
Analysis: m.p.: over 250° C
$C_8H_9NO_4$ mol. wt. 183.9.

|  | theoretical | found |
|---|---|---|
| C% | 52.46 | 52.50 |
| H% | 4.95 | 4.80 |
| N% | 7.65 | 7.66 |
| O% | 34.95 | 35.05 |

The IR spectra, NMR and mass-spectra confirmed the above structure.

EXAMPLE III

Methylglyoxal-succinimide

N-(2-keto-propane-1ol)-2,5diketo pyrrolidine

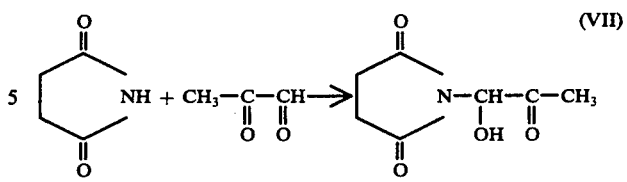

9.9 g of succinimide were added to 100 ml of water containing trace amounts of $K_2CO_3$. The mixture was then heated to 70° C while stirring. When all solid had dissolved, 20 ml (8.0 g) of a 40% aqueous methylglyoxal were added in one batch and the reaction mixture was kept at 70° C for another hour.

During the heating the yellow reaction mixture darkened to a reddish-brown color.

At the end of the reaction time the solution was filtered through folded paper, cooled to room temperature and concentrated to about 15 ml in a vacuum.

During the concentration crystals separated which were collected and washed carefully with a small volume of ice water because of high water solubility.

The mother liquor was further concentrated in a vacuum and a second crop of crystals were collected as above.

The combined crystalline crops were purified on recrystallization from a small volume of hot water. The collected crystals were washed with a small volume of ice-water and finally dried over $P_2O_5$ at 40° C in a vacuum.

Yield: 9.85 g (57.6% of the theoretical)
Analysis: m.p. 111°–112° C
$C_7H_9NO_4$ molecular weight 171.2

|  | theoretical | found |
|---|---|---|
| C% | 49.12 | 49.09 |
| H% | 5.30 | 5.31 |
| N% | 8.18 | 8.10 |
| O% | 37.39 | 37.36 |

The IR spectra, NMR and mass spectra confirmed the structure as above.

EXAMPLE IV

Methylglyoxal-phthalimide

N'-(2-keto-propane-1-ol)-1,3-isoindoledione. Reaction:

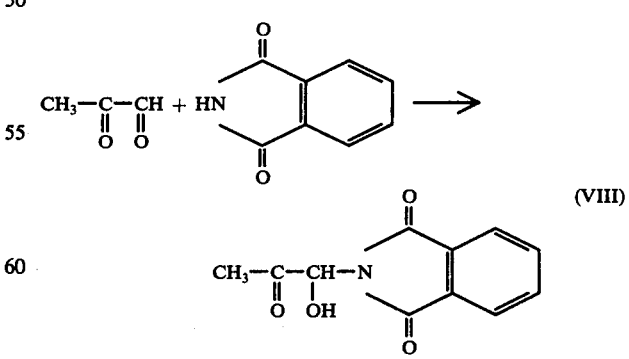

14.7 g of phthalimide were suspended in 400 ml of 50% v/v aqueous p-dioxane and the pH of the suspension was adjusted to 5.5 with alkali (KOH) and a trace amount of $K_2CO_3$ added. The mixture then was heated to 70° C under mechanical stirring. When all solid was dissolved, 20 ml (8.0 g) of 40% aqueous methylglyoxal was added in one batch and the reaction mixture was kept at 70° C for another 4 hours while stirring.

The reaction mixture darkened to a reddish-brown color during the reaction.

At the end of the reaction time the solution was filtered through folded paper, cooled to room temperature and concentrated to about ⅓rd of its original volume in a vacuum. During concentration the crystals that formed after brief cooling to 2° C were separated and collected. The crystals were recrystallized twice from hot water. Finally, the crystals were dried over $P_2O_5$ in a vacuum at 40° C.

Yield: 9.73 g (39.7% of theoretical)
Analysis: m.p.: 224°–226° C.
$C_{11}H_9NO_4$ — mol. wt. 219.2

|  | theoretical | found |
|---|---|---|
| C% | 60.28 | 60.22 |
| H% | 4.14 | 4.16 |
| N% | 6.39 | 6.40 |
| O% | 29.20 | 29.23 |

UTILITY

The compounds of the invention are useful as antineoplastic, antibacterial and antiviral compounds and, because of the blocking of the protein synthesis, generally as inhibitors of the rejection mechanism of the body occurring in transplantation of tissue and organs.

They are also useful as radiosensitizers where they may be used as potentiating compounds in connecting with a radiation treatment.

Their use may be combined with the co-administration of adjuvants such as antihistamines, 2,4-dioxovaleric acid, oxamates, menadiol-diphosphates, serotonine, etc.

The compounds can be used by injection, that is by subcutaneous, intraperitoneal, intravenous injection or by infusion or perfusion. The average daily dose with methyl glyoxal maleimide as determined with mice is about 1.8 to 7.5 mg/kg for intraperitoneal and subcutaneous injection. The corresponding range for methylglyoxal glutaconic imide is about 250 to 1020 mg/kg in mice. These values can be converted for other species by using a conversion chart which is based on the equivalent body surface, and this establishes the "area-dose" relation (Freireich, E. J. et al.: Can. Chem. Therap. Rep. 50, p. 219, 1966). From the chart the following conversion factors expressed in mg/kg can be obtained:

| mouse to mouse (20g) | factor 1.0 |
| mouse to rat (150 g) | factor 1/2 |
| mouse to monkey (3 kg) | factor 1/4 mg/kg |
| mouse to dog (8 kg) | factor 1/6 |
| mouse to man (60 kg) | factor 1/12 |

For instance, if a given dose in mouse is 50 mg/kg, the appropriate dose in monkey will be (50× 1)/4 = 13 mg/kg. On this basis the 1.872 mg/kg dose level of methylglyoxal-maleimide on mouse will be (1.872× 1)/12 = 0.156 mg/kg or 0.156× 60 = 9.36 mg per 60 kg man/day.

Pharmaceutical compositions useful for injection purposes were prepared as follows:

The oven dried solids were weighed and the required amount was dissolved in physiological saline. Alternatively the quantity was dissolved in 95% ethanol or acetone and the resulting solution was diluted to the final volume with physiological saline in such a way that the final concentration of alcohol did not exceed 2% v/v or with acetone did not exceed 5% v/v.

The pH of the injectables was between 5.6 and 6.2. (Alkaline and acidic pH have to be avoided as the latentiated derivatives decompose readily).

The following is a specific example:

Methylglyoxal-maleimide was dissolved at a final concentration of 48.67 μg/ml in physiological saline for treatment of mice. From this solution 1.0 ml was injected intraperitoneally to each animal on each day. This amount was equivalent to 1.872 mg/kg at an average body weight of 26±3 grams of mice.

For the subcutaneous treatment the same volume as indicated above was used but injected on two sites, that is 0.5 ml on each site of mice.

Higher dose levels than 1.872 mg/kg were made up in the same manner as indicated above. They of course contained more of the compound than 48.67 μg/ml.

The principal diluent (excipient) was physiological saline with ethanol or acetone as diluent are also useful, but saline as such is the preferred diluent if the solubility of the compound therein is adequate.

BIOLOGICAL EVAULATION

I. COMBATTING REJECTION MECHANISM

Skin grafting in mice is well established and this tissue is among the most sensitive indicators of histocompatibility differences. The retnetion of skin graft between genetically non-related mice is an excellent method of evaluating activity against rejection mechanism. p As the rejection of transplants is associated with antigen formation against the incompatible proteins of the donated tissue, a drug which specifically represses the protein synthesis without affecting the intermediary metabolism of the host is a potential candidate for combatting rejection.

The experiments described here were performed on random-bred Swiss albino mice (white, females, average body weight 26±3 g; Charles River CD-1-strain) and inbred C3HStCrl mice (cinnamon gray, females, average body weight 20±2 grams; Charles River pedigreed breeders from L. C. Strong Foundation) and othotopic skin transplants were made in both ways, that is, white to gray and gray to white.

Standard transplantation technique (R. E. Billingham, W. K. Silvers in Transplantation of tissues and cells, The Wistar Institute Press, Philadelphia, p. 8, 1961) was utilized: From nembutal anesthetized animals 4–6 "pinch"-grafts (full thickness, 3–4 mm in diameter) of the close clipped and sterilized skin were collected from the thorax and immediately transplanted. The grafts were positioned in the "beds" (in place of the pinch-graft) and were held in position by tulle gras (vaseline-impregnated gauze) and by plaster-of-Paris impregnated bandage around the thorax.

The bandages were removed on the 6–9th day after the transplantation and the future development of the grafts was followed by macroscopical observations.

Positive and negative controls were made simultaneously for skin rejection:

a. Four positive control isografts (white to white, and gray to gray) were made. They showed a confluence and union of the fitted grafts with the surrounding skin and beds in 7-10 days. On the 21-28th day the fur-bearing skin had regenerated a completely new crop of hairs indistinguishable from the original population with respect to colors, density and orientation.

b. Four negative control heterografts (white to gray and gray to white) were made without treatment. They showed no confluence and union with the surrounding tissue which was locally inflamed. On the 10-12th day after transplantation intravascular thrombies, capillary ruptures, extravasation of blood were the first signs that the grafts were heading for necrosis and rejection which occurred on the 18-25th day.

The heterografts with treatment followed three courses with methylglyoxal-maleimide (at dose level 3.744 mg/kg/animal/day) administered intraperitoneally in a total amount of 1.0 ml/animal/day.

i. Animals were treated for 10 days with the composition before grafts were exchanged and treatment was discontinued on the day of transplantation.

ii. Animals were not treated before the grafts were exchanged but the treatment started on the day of transplantation and continued for 10 days.

iii. Animals were treated for 10 days with the drug before the grafts were exchanged and the treatment schedule was continued for 25 days after the transplantation.

Histological examination was performed on normal and tumorous mice organs (i.e., tumor, liver, spleen, kidney, heart, intestine) on the 11th day after ten consecutive daily subcutaneous or intraperitoneal treatments.

SET-UP OF EXPERIMENTS

The test solutions were prepared by dissolving either 38.72 mg of methylglyoxal maleimide ("A") or 5278 mg of methylglyoxal glutaconic imide ("B") in 100 ml of physiological saline. The pH of the solution was adjusted to 6.0, sterilized on Millipore filtration and stored in sterile vials at about 10° C. One millimeter of such solutions contained 0.387 mg of compound "A" or 52.78 mg of compound "B", respectively and when injected into mice of an average weight of 26 grams the dose was equivalent to 14.884 mg/kg of the compound "A" and 2030 mg/kg of the compound "B".

Random-bred Swiss albino mice (Charles River CD-1 strain, average weight 26±3 g, females) were inocculated with 25 million Sarcoma-180 cells (in about 0.25 ml of ascitic fluid, cell age 7 days) on the right scapular region. The animals were randomized on the 4th day after the inoculation with the cancer cells, placed in separate test groups of 10 mice per group (5 mice/cage) and weighed.

RESULTS

| Assay | No of mlcc | Graft* | Treatm+ | Results |
|---|---|---|---|---|
| Positive control | 10 10 | w to w<br>g to g | no<br>no | 100% take in 21-28 days |
| Negative control | 10 10 | w to g<br>g to w | no<br>no | 100% rejection in 10-25 days |
| (i) Pretreatm. for 10 days | 10 10 | w to g<br>g to w | yes<br>yes | 30% rejection on 26-30 days<br>100% rejection on 31-40 days |
| (ii) Post graft treatm. for 10 days | 10 10 | w to g<br>g to w | yes<br>yes | 10% rejection on 26-30 days<br>60% rejection on 31-40 days |
| (iii) Pretreatm. for 10 days and post graft treatm. for 25 days | 20 20 | w to g<br>g to w | yes<br>yes | No rejection on 26-30 days<br>10% rejection on 31-40 days |

+Treatment: daily injection with 3.744 mg/kg methylglyoxal-maleimide in 1.0 ml saline by intraperitoneal route / mouse / day
*the w stands for white mice (Swiss albino, randombred, Charles River CD-strain
the g stands for cinnamon gray mice (C3HStCrol, inbred strain)
Note: per cent figures in Results are cummulative values.

II. Action on Tumors

The biological effects of methylglyoxal maleimide ("A") and methylglyoxal glutaconic imide ("B") were determined by tests on normal (non-tumorous) and subcutaneous Sarcoma-180 tumor-bearing mice. The acute toxicity (mortality), the maximum tolerated dose at 10% lethality ($LD_{10}$), the effective dose at 90% effectiveness ($ED_{90}$) and the corresponding therapeutic index ($LD_{10}/ED_{90}$) were determined for ten day consecutive (daily) treatment. The compounds were administered by intraperitoneal route and the values were calculated by standard methods (Goldin A., in Meth. Can.Res. 4, p. 193, 1968).

A thirty-day survival test was carried out with normal mice to determine any possible delayed toxicity.

Normal, non-tumor-bearing mice of the same strain, sex and weight were also randomized and placed in separate test groups.

The compositions were injected at different dose levels, each dose being double the next-lower dose, with three test groups (30 mice) for each dose level. The injection was effected intraperitoneally into normal and tumor-bearing mice, starting on the fourth day after the inoculation with cancer, once daily for ten consecutive days. The volume of the injection at each dose level was brought up to 1.0 ml with saline. A proper number of normal and tumorous mice was treated with saline solution in the same manner, frequency and volume as a control experiment. The body weight change and mortality (acute toxicity) were recorded daily.

On the eleventh day (tumer age 14 days) the test and control mice were sacrificed, the tumor or tumorous area was cut out, weighed and stored in formaldehyde for histological examination. At the same time the liver, kidneys, spleen, heart, and a piece of the small intestine were collected and stored in formaldehyde for histopathological evaluation of the effect of the drugs on these tissues and organs.

The anti-neoplastic action of the drugs was assayed by comparison of the tumor weight present in treated and control animals and expressed as the percent of controls average weight (T/C%). The presence of malignancy in the tumors or tumor-areas of the treated animals was verified by histological examination.

The reabsorption of tissue, formed between the inocculation of the cancer cells and the onset of the treatment is relatively slow. Treated animals even under strong cancerostatic action of the drugs show a small quantity (100–200 mg) of tissue in the area where the tumor cells where deposited. It is therefore difficult to tell the nature of these residual tissues by macroscopic examination. Most of these residual "lumps" are made up of connective tissues and necrotic, scar tissues. If it were regarded as neoplasia without histological examination the T/C% calculation would give an erratic result in the evaluation of the anti-cancer action of the compound. Histological examination of these "lumps" therefore is exceedingly important in order to arrive at a valid evaluation of the effectiveness of the drugs especially in short-term experiments (10 days) as carried out in the present assays. Hence, the histological findings, supplementing the actual weight of the residual weight, were used as final verdict of the effectiveness.

A number of normal animals treated with the drugs in the same manner as the tumorous ones were also sacrificed on the eleventh day, and their organs were collected for histological examination. Groups of normal treated animals were also observed for 30 days for delayed toxicity effects and compared to non-treated controls.

RESULTS

From the mortality, toxicity and anti-tumor effects obtained in the in-vivo experiments with mice outlined above, the $LD_{10}$, $ED_{90}$ and the IT of compounds "A" and "B" were calculated for intraperitoneal administration of the drugs. The results are detailed in Tables I and II. As will be seen, both compounds have a potent anti-neoplastic effect on subcutaneously transplanted Sarcoma-180 of mice. The effect is a direct anti-tumor action and is not due to "anti-host effect" (caloric-restriction), as evidenced by no significant weight change of mice during treatment.

The residual "tumor weight" of the treated animals was considerably less than that of the controls, and histopathological examination showed that these "lumps" were free of cancerous growth.

Regarding the effects of the two compounds on the organs of mice (liver, spleen, kidney, heart, small intestine, and bone marrow) no abnormalities were found. Part of the compounds were excreted with the urine.

The white blood cell count (WBC) sharply increases shortly after the administration of the compounds into tumor-bearing mice indicating the activation of the reticulo-endothelial-system (RES) due to the massive destruction of the neoplastic tissues.

Tables 1 and 2 show the results with methylglyoxal-maleimide (A) and methylglyoxal-glutaconic imide (B) on tumorous and non-tumorous mice.

Table 1

The Effect of Methylglyoxal-maleimide (A) on Normal and Tumorous Mice
Daily intraperitoneal injections for 10 days

| mg/kg | NORMAL M%+ | NORMAL Δ body wt | TUMOROUS M%+ | TUMOROUS Δ body wt. | ED% |
|---|---|---|---|---|---|
| 14.896 | 100 | — | 100 | — | |
| 7.488 | 0 | −0.2 | 0 | +0.1 | 100 |
| 3.744 | 0 | +0.1 | 0 | +0.3 | 100 |
| 1.872 | 0 | +0.39 | 0 | +0.4 | 100 |
| 0.936 | 0 | +0.46 | 0 | +0.6 | 60 |
| 0.468 | 0 | +0.7 | 0 | +0.65 | ~1 |
| 0.234 | 0 | +1.0 | 0 | +0.96 | >0.5 |

$LD_{10}$ 8.59mg/kg
$ED_{99}$ 1.15 mg/kg
IT 7.46

+M% stands for per cent mortality in 10 days. The 30 day mortality rate of all of the treated nontumorous animals was identical. The average weight of all test mice was 26.3 grams. The mortality (M%) presented in the table is related to a total volume of 1.0 ml/animal/day at each mg/kg dose levels. The reduction in the total volume of injection causes an increase in mortality.

Table 2

The Effect of Methylglyoxal-glutaconic imide (B) on Normal and Tumorous Mice
Daily intraperitoneal injections for 10 days

| mg/kg | NORMAL M%+ | NORMAL Δ body wt | TUMOROUS M%+ | TUMOROUS Δ body wt | ED |
|---|---|---|---|---|---|
| 2032 | 100 | — | 100 | — | |
| 1524 | 50 | −0.4 | 40 | — | |
| 1016 | 0 | −0.1 | 0 | −0.3 | 100 |
| 508 | 0 | −0.1 | 0 | +0.1 | 100 |
| 254 | 0 | +0.15 | 0 | +0.4 | 100 |
| 127 | 0 | +0.3 | 0 | +0.35 | 55 |
| 63.5 | 0 | +0.55 | 0 | +0.6 | >5 |

$LD_{10}$ 1310 mg;kg
$ED_{90}$ 210 mg/kg
IT 6.23

+M% stands for per cent mortality in 10 days. The 30 day mortality rate of all the treated nontumorous animals was identical. The average weight of all test mice was 26+ 3 grams. The mortality (M%) presented in the table is related to a total volume of 1.0 ml/animal/day at each mg/kg dose levels. The reduction in the total volume of injection causes an increase in mortality.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. The compound, which is N'-(2-keto-propane-1-ol)-2,5-dioxo-pyrroline-3-ene.
2. The compound, which is N'-(2-keto-propane-1-ol)-2,6-dioxo-pyridine.

* * * * *